United States Patent
Ruben et al.

(10) Patent No.: US 10,308,625 B1
(45) Date of Patent: *Jun. 4, 2019

(54) EXTRACTION OF CANNABIDIOL

(71) Applicants: Aari Ruben, Tucson, AZ (US); Robin James Bach, Tucson, AZ (US)

(72) Inventors: Aari Ruben, Tucson, AZ (US); Robin James Bach, Tucson, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/932,630

(22) Filed: Mar. 28, 2018

(51) Int. Cl.
*C07D 311/80* (2006.01)
*C07C 37/70* (2006.01)

(52) U.S. Cl.
CPC ............ *C07D 311/80* (2013.01); *C07C 37/70* (2013.01)

(58) Field of Classification Search
CPC .................................................... C07D 311/80
USPC .......................................................... 435/410
See application file for complete search history.

(56) References Cited

U.S. PATENT DOCUMENTS 9,950,275 B1 * 4/2018 Ruben ................... B01D 11/04

* cited by examiner

*Primary Examiner* — Taofiq A Solola
(74) *Attorney, Agent, or Firm* — Mark Ogram

(57) ABSTRACT

The invention is methodology of producing a variety of cannabis derivatives such as THC, CBD, Delta-11, and budder. The technique involves the steps of: grinding a whole cannabis plant, including the root ball thereof, freezing the ground plant, soaking the frozen ground plant in a selected solvent, and, removing the solvent, thereby producing desired derivative of cannabis. Solvents include coconut oil, olive oil, vegetable oils, avocado oil, and seed oils.

5 Claims, 1 Drawing Sheet

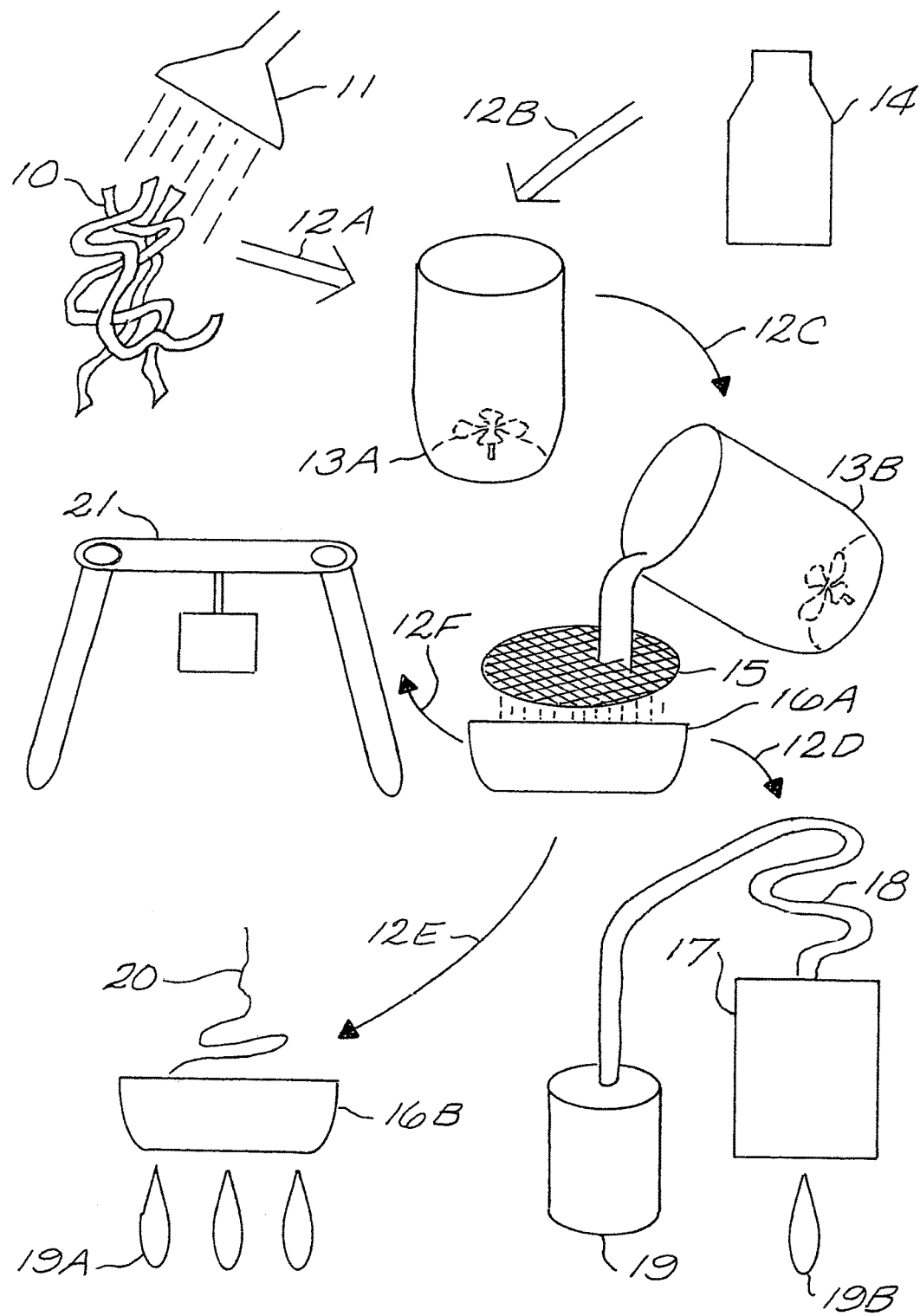

EXTRACTION OF CANNABIDIOL

This is a continuation of U.S. patent application Ser. No. 15/731,103 filed on Apr. 18, 2017, and entitled "Extraction of Cannabidiol", now U.S. Pat. No. 9,950,275, issued on Apr. 24, 2018, which was a continuation-in-part of U.S. patent application Ser. No. 14/756,823, filed on Oct. 19, 2015, entitled "Extraction of Cannabidiol.

BACKGROUND OF THE INVENTION

This invention relates generally to cannabis and more particularly to the extraction of Cannabidiol (CBD).

Cababidiol is one of many active cannabinoids identified in cannabis. It is a major phytocannabinoid and accounts for up to 40% of the plant's extract. Further, CBD is considered to have a wider scope of medical application than tetrahydrocannabinol (THC). Unlike THC, CBD is considered to be non-psychoactive. A liquid form of CBD is used for the treatment of Dravet syndrome.

While early use of cannabis relied on rudimentary, if any, refining of the plant, the modern science in the field recognizes that there are abundant different cannabinoids which have varying affects and treatment modalities. Because of this, a variety of techniques have been developed to extract different cannabinoids from the leaves and stems of the marijuana plant.

There is a constant and growing need to obtain different cannabinoids so that patient treatment can be enhanced.

SUMMARY OF THE INVENTION

While common root balls from the cannabis plant are normally seen as waste, the present invention provides for a method of extracting various cannabinoids from the root ball.

The initial step is to clean the root balls using water. This process is enhanced with a tumbling action and repeatedly refreshing the water. Once fully cleaned, the root ball is ground into a powder ideally in the 10-50 mesh range. This mesh size provides for particle size allowing for efficient extraction of the cannabinoid.

The process is to grind the washed root balls into a paste (if moisture is still present) or "flour like" (if the cleaned root ball has fully dried) consistency, then combine with chosen solvent. Depending on extraction technique used, the process varies; the preferred methodology is to use a slightly heated solvent/root ball powder combination.

Those of ordinary skill in the art readily recognize a variety of refining techniques which can be used in this context, including, but not limited to those described in: U.S. Pat. No. 8,735,111, entitled "Processes for Producing Hydrocarbon Products" issued to Vanhercke et al. on May 27, 2014; U.S. Pat. No. 8,809,026, entitled "Process for Producing Lipids" issued to Vanhercke et al., on Aug. 19, 2014; and, U.S. Pat. No. 9,061,992, entitled "Process for Producing Hydrocarbon Products" issued to Vanhercke et al., on Jun. 23, 2015; all of which are incorporated hereinto by reference.

In this context, the ground root ball is combined with an solvent to assist in the separation of the cannabinoid from the plant particles. Some of the more common solvents provide for concentration of hydrogen (hydrogenization). Some of the solvents are coconut oil, grape seed oil, carbon dioxide, butane, and grain alcohol.

Other solvents include chloroform, petroleum ether, benzene, ethanol, methanol, isopropanol, and methylene chloride. Ideally the extraction and concentration is performed using a standard reflux arrangement in which the flask containing the material is heated and then cooled using a reflux head.

In this context, the solvent with the ground root ball material is mildly heated allowing the warm solvent to gradually extract the cannabinoids. The extracted cannabinoid oil vaporizes and then condensed to obtain the concentrate.

The extracted cannabinoid oil is optionally purified using benzene, petroleum, or ether with water. The top layer of this mixture contains the sought after cannabinoids by skimming the mixture.

The preferred methodology uses a simple sieve to extract the plant particles from the liquid cannabinoid. This preferred method of using alcohol or oil with extraction being achieved by manual agitation, stirring/mixing the products, then manually separating the liquids and solids through a sieve, cheesecloth, or filter papers. The resulting concentrate can then be refined by boiling off the alcohol.

When a closed loop extraction using carbon dioxide, butane, or another supercritical solvent, the machine is used to separate the active compounds from the organic material. The resulting oil is then refined by heat and pressure to eliminate residual solvent.

The resulting products can be used as a dietary supplement or as a supplement to increase CBD content of traditional cannabis extracts.

Those of ordinary skill in the art readily recognize a variety of uses the extraction may be used for patient treatment, including, but not limited to those described in: U.S. Pat. No. 6,132,724, entitled "Allelic Polygene Diagnosis of Reward Deficiency Syndrome and Treatment" issued to Blum on Oct. 17, 2000; and, U.S. Pat. No. 8,309,595, entitled "Hyrdazone Modulators of Cannabinoid Receptors" issued to Attala et al. on Nov. 13, 2012; and, U.S. Pat. No. 9,079,854, entitled Hydrazone Modulators of Cannabinoid Receptors" issued to Attala et al. on Jul. 14, 2015; and of which are incorporated hereinto by reference.

The invention together with various embodiments will be more fully explained by the accompanying drawings and the following descriptions thereof.

DRAWINGS IN BRIEF

FIG. 1 diagrams the process of the present invention.

DRAWINGS IN DETAIL

FIG. 1 diagrams the process of the present invention, a method of extracting cannabinoid.

Root ball 10 is obtained and is repeatedly cleaned using water 11. This step is to remove any debris such as dirt and chaff from the root ball itself. The now cleaned root ball is placed in a grinder type of mechanism 13A and is ground into a powder. Additionally, a solvent 14, as describe above is added to the dry powder and a mixture is produced.

This mixture 13B is poured through sieve 15 such as cheese cloth material to remove any suspended particles. The "purified" mixture is collected 16A.

Depending on the process being employed, the "purified" mixture is subjected to heat 19B while in a container 17, thereby evaporating the solvent and desired cannabinoi which is condensed 18 and collected 19.

Another process simply heats 19A. This produces a "purified" mixture 16A as the solvent evaporates 20A, leaving behind the cannabinoid. The resultant residue is then chilled to create an enhanced concentrate.

In yet another refining process, the "purified" mixture is subjected to a centrifuge 21 to create an enhanced concentrate. After the process of applying centrifugal forces on the cannabinoid concentrate, the waste solvent is removed.

In this manner, the cannabinoid obtained from the root is now useful for additives to provide the desired enhancement of the treatment being administered.

This methodology illustrated in FIG. 1 is also used to develop specific derivatives of cannabis such as THC, CBD, and Delta-11. By altering the chemicals used and the steps themselves, the same technique is tailored for specific derivatives.

In one such tailoring the whole cannabis plant, including the root ball, is ground 13A and is then frozen (ideally using liquid nitrogen or carbon dioxide) to separate the sought-after derivative from the ground plant. When the solvent (and sometimes water) is removed (typically by evaporation), the residue has a high concentration of the derivative.

To enhance the procedure, the plant being ground ideally already has enhanced characteristics, such as THC, CBD, or Delta-11.

The solvent chosen for the process is ideally chosen from the group consisting of coconut oil, olive oil, vegetable oils, avocado oil, and seed oils. These solvents have been shown to produce exceptional results in the refining process.

In the case of CBD, the solvent is from the group consisting of butane, hexane, ethanol, and butanol.

In some application, where a budder is sought, pressure and heat is applied to assist in the separation process. In this context, pressure greater than 15 psi and heating (in the range of 190-265 degrees Fahrenheit) the frozen ground plant for a period between forty-five minutes and three hours. The budder so produced is a valuable derivative of cannabis.

To assist in the process, and to enhance the solvent removal the soaked mixture 13B is passed through a mesh screen 15 to remove plant parts. In this context, the mesh screen has a screen size of 160-220 microns.

When CBD is being obtained, the heat applied is less than one hundred twenty degrees Fahrenheit.

It is clear that the present invention provides for an enhanced source for obtaining different cannabinoids so that patient treatment can be enhanced.

What is claimed is:

1. A method of producing a refined delta-11 in cannabis consisting essentially of:
   a) grinding a cannabis plant chosen for its delta-11 levels;
   b) freezing the ground cannabis;
   c) soaking the frozen ground cannabis in a solvent;
   d) simultaneously applying pressure greater than 15 pounds per square inch and heating the frozen ground cannabis in the coconut oil in the range of 190-265 degrees F. for a period of between 45 minutes and 3 hours, thereby yielding a delta-11 cannabis budder; and,
   e) passing the delta-rich cannabis budder through a mesh screen to remove cannabis plant parts, thereby producing the refined delta-11 cannabis.

2. The method of producing a refined delta-11 in cannabis according to claim 1, further including the step of choosing the solvent for soaking the frozen cannabis from the group consisting of coconut oil, olive oil, vegetable oils, avocado oil, and seed oils.

3. The method of producing a refined delta-11 in cannabis according to claim 2, wherein the step of passing the delta-rich cannabis budder through a mesh screen to remove plant parts includes selecting a mesh screen having a mesh size of 160-220 microns.

4. The method of producing a refined delta-11 in cannabis according to claim 2, wherein the step of freezing the ground cannabis plant includes the step of applying carbon dioxide to the ground cannabis.

5. The method of producing a refined delta-11 in cannabis according to claim 2, wherein the step of grinding the cannabis plant comprises the step of grinding the root ball of the cannabis plant.

* * * * *